(12) United States Patent
Hamidian Jahromi et al.

(10) Patent No.: US 10,376,618 B2
(45) Date of Patent: Aug. 13, 2019

(54) THORACIC CATHETER DEVICE

(71) Applicants: Alireza Hamidian Jahromi, Shreveport, LA (US); David Hilton Ballard, Shreveport, LA (US); Jeffery Adam Weisman, West Monroe, LA (US); Horacio Ruben Vincent D'Agostino, Shreveport, LA (US)

(72) Inventors: Alireza Hamidian Jahromi, Shreveport, LA (US); David Hilton Ballard, Shreveport, LA (US); Jeffery Adam Weisman, West Monroe, LA (US); Horacio Ruben Vincent D'Agostino, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/518,318

(22) PCT Filed: Oct. 29, 2015

(86) PCT No.: PCT/US2015/057937
§ 371 (c)(1),
(2) Date: Apr. 12, 2017

(87) PCT Pub. No.: WO2016/069829
PCT Pub. Date: May 6, 2016

(65) Prior Publication Data
US 2017/0304508 A1    Oct. 26, 2017

Related U.S. Application Data

(60) Provisional application No. 62/072,075, filed on Oct. 29, 2014.

(51) Int. Cl.
*A61M 1/00* (2006.01)
*A61M 25/00* (2006.01)
*A61M 27/00* (2006.01)

(52) U.S. Cl.
CPC .......... *A61M 1/008* (2013.01); *A61M 1/0001* (2013.01); *A61M 25/0068* (2013.01); *A61M 27/002* (2013.01); *A61M 2210/101* (2013.01)

(58) Field of Classification Search
CPC .............. A61M 1/0001; A61M 1/008; A61M 2210/101; A61M 25/0068; A61M 27/002
See application file for complete search history.

(56) References Cited

U.S. PATENT DOCUMENTS

| | | | |
|---|---|---|---|
| 4,567,880 A | 2/1986 | Goodman | |
| 5,433,705 A * | 7/1995 | Giebel | A61M 25/0017 604/265 |

(Continued)

OTHER PUBLICATIONS

Jamshid H. Karimov et al., "Incidence of chest tube clogging after cardiac surgery: a single-centre prospective observational study", European Journal of Cardio-Thoracic Surgery 44, Mar. 21, 2013 pp. 1029-1036.

(Continued)

*Primary Examiner* — Imani N Hayman
(74) *Attorney, Agent, or Firm* — Davis & Bujold PLLC; Michael J. Bujold (57) ABSTRACT

A thoracic catheter system comprises a flexible thoracic catheter for inserting into a thoracic cavity of a human. A distal end of the thoracic catheter has a plurality of apertures. A proximate end of the thoracic catheter is designed to extend out of the thoracic cavity. A three way valve is one of fused with and removably attached to the proximal end of the thoracic catheter.

19 Claims, 13 Drawing Sheets

(56) References Cited

U.S. PATENT DOCUMENTS

| | | | |
|---|---|---|---|
| 5,554,138 A | 9/1996 | Stanford et al. | |
| 6,827,701 B2 | 12/2004 | MacMahon et al. | |
| 2002/0091352 A1* | 7/2002 | McGuckin, Jr. | A61M 1/285 |
| | | | 604/29 |
| 2005/0085769 A1 | 4/2005 | MacMahon et al. | |
| 2008/0065051 A1 | 3/2008 | Williams | |
| 2009/0005760 A1 | 1/2009 | Cartledge et al. | |
| 2009/0227987 A1 | 9/2009 | Singer | |
| 2013/0150701 A1 | 6/2013 | Budar et al. | |

OTHER PUBLICATIONS

Shanaz Shalli, M.D. et al., "Chest Tube Selection in Cardiac and Thoracic Surgery: A Survey of Chest Tube-Related Complications and Their Management", Wiley Periodicals, 2009, pp. 503-509.
International Search Report Corresponding to PCT/US2015/057937 dated Feb. 2, 2016.
Written Opinion Corresponding to PCT/US2015/057937 dated Feb. 2, 2016.

* cited by examiner

FIG. 12

THORACIC CATHETER DEVICE

CROSS REFERENCE TO RELATED APPLICATIONS

This application claims priority to U.S. Provisional Patent Application No. 62/072,075 filed Oct. 29, 2014, the contents of which are incorporated herein by reference in its entirety.

STATEMENT REGARDING FEDERALLY SPONSORED RESEARCH OR DEVELOPMENT

Not applicable.

FIELD OF THE INVENTION

The present invention generally relates to thoracic catheters. The present invention further relates to medical imaging, drug delivery, and fluid control devices.

BACKGROUND OF THE INVENTION

The use of thoracic catheters (also referred to as a chest drain, chest tube, intercostal drain, tube and tube thoracostomy) is widely known, and became popular after the widespread use during the World War II and the Korean War. A thoracic catheter is known as a flexible/semi-flexible tube which is inserted into the chest cavity (pleural and/or pericardial space) and is used to remove/evacuate air (pneumothorax) or fluids (blood, effusion, chyle or pus) from such cavities.

Common indications for thoracic catheter insertions include but are not limited to presence of pneumothorax, tension pneumothorax, large pleural effusions, chylothorax, hemothorax, and empyema. Thoracic catheters are frequently used in the postoperative setting following a thoracotomy, esophagectomy, video-assisted thoracoscopy surgery ("VATS") and cardiac surgeries. Once the thoracic catheter or chest tube is in place, it is sutured or otherwise attached to the skin to prevent movement. The chest tube is then connected to the drainage container (e.g., a canister) using additional tubing and connectors. The canister may also be connected to a suction source (e.g., negative 20 cm of water pressure) or it may be left on a water seal.

Drainage of the pleural space by means of a thoracic catheter is the most common intervention in thoracic trauma, and there are more than one million thoracic catheters that are placed annually in the United States.

Despite the fact that thoracic catheters are used quite commonly worldwide, an ideal functioning design for the device has proven thus far stubbornly elusive, regardless of the significant market forces motivating such an improvement. The most frequent complication associated with a thoracic catheter is clogging or blockage of the catheter lumen by thrombus formation or debris that is inside the catheter lumen. This clogging can cause major subsequent complications and non-functioning or malfunctioning of the tube. The presence of a clot inside the catheter lumen can also cause stasis of the drainage, cause infections and/or deterioration of infections (e.g., in cases with empyema). One prospective study reported a thirty-six percent rate of clogging and non-functioning of the thoracic catheter in patients undergoing cardiac surgeries. [J. R. Karimov, et al. Incidence of chest tube clogging after cardiac surgery: a single-centre prospective observational study. *Eur. J. Cardiothorac. Surg.* 44(6):1029-36 (2013).] This complication was reported to be more common in urgent procedures and/or reoperations and in cases with increased intra-operative blood transfusions. Such clogging was also associated with a higher risk of atrial fibrillation development in the patient, which could potentially be a lethal complication. Interestingly, more than eighty percent of the clogging in the thoracic catheter was found to be in the internal portion of the tube (i.e., the non-visible or intra-thoracic portion that is inside the patient's chest cavity), which makes the diagnosis of this complication by bedside visualization and or inspection very difficult or impossible.

Due to the same reason, management of this complication can be complex and challenging. The thoracic catheter can become clogged at any time after its placement, and it is known that clinicians generally underestimate the prevalence of this failure to drain. Clogging of the tube can even become life threatening in cases where bleeding in the chest goes undiagnosed due to lack of drainage. When a thoracic catheter clogs, it can cause accumulation of blood around the heart (pericardial tamponade) and the lungs (hemothorax). In case of the pneumothorax, blockage in the thoracic catheter can cause tension pneumothorax, which is life threatening.

In a survey which included North American cardiothoracic surgeons and specialty cardiac surgery nurses, 100% of the responders confirmed that they have had problems with thoracic catheters getting clogged and (87%) reported adverse patient outcomes from a clogged tube. [S. Shalli, et al. Chest tube selection in cardiac and thoracic surgery: a survey of chest tube-related complications and their management. *J. Card. Surg.* 24(5):503-9 (2009).] More than 50% of the participants confirmed that they are not satisfied with currently available chest tubes and procedures to avoid chest tube occlusion. Some of the responders even mentioned that they forbid the current technique for unclogging thoracic catheters, namely the stripping, tapping, and/or squeezing maneuver, for fear of causing more bleeding by the negative pressures generated. In addition, the survey respondents noted that patients experience increasing discomfort with increasing drain size and did not think that increasing the size of the thoracic catheters was a good strategy to prevent clogging of the tubes. The conclusion of the survey highlighted the frequent clogging problems with current postsurgical chest drainage systems and observed a pressing need for new and innovative solutions to prevent clogging complications and to address clinician concern and patient pain.

Another challenge with the current thoracic drainage system is when a patient who already has a thoracic catheter in place requires a video-assisted thoracoscopic surgery ("VATS") procedure. For the VATS operation, in the current practice, the surgeon is taught to make additional incisions ("port sites") and insert ports, which are used for entry of a camera and instruments. The inventors noted that a single incision VATS, which would spare the patient from having extra incisions and/or port insertions while undergoing VATS would be ideal, as it would decrease postoperative pain and result in a higher patient satisfaction compared with the conventional three-port VATS. The inventors also realized that a thoracic catheter should be designed that could also function as the lone port for a single incision VATS, which would spare the patient even from a single extra port. Outside experts in the field of thoracic catheters have expressed skepticism of single incision VATS due to current technological limitations.

As the above description clearly shows, there is a long felt and unresolved need for a better designed thoracic catheter, including methods and devices to help detect and/or prevent blockages in such catheters and providing the capability to use such catheters as port site when performing VATS procedures.

SUMMARY OF THE INVENTION

Wherefore, it is an object of the present invention to overcome the above mentioned shortcomings and drawbacks associated with the prior art.

Another object of the present invention is to provide a thoracic catheter comprising a disposable flexible or semi-flexible tube with a plurality of side holes disposed on a distal end. A three way valve is preferably fused and/or removably attached to a proximate end of the catheter. The distal end of the tube is inserted into the chest (thoracic) cavity to, inter alia, evacuate fluid and/or air, sample tissue, or act as a port in video assisted thoracoscopy surgery.

A further object of the present invention is to provide a thoracic catheter device that may also be used as a drug delivery device for anticoagulants, antibiotics, and chemotherapeutics, as a delivery device for contrast for medical imaging, for a plethora of existing interventional radiology procedures that utilize thoracic catheters or access to the thoracic cavity, for pleurodesis, for access to the mediastinum as an alternative approach for mediastinoscopy, and as a port of entry video-assisted thoracoscopy surgery.

Among the many advantages of the disclosed novel design is the ability to directly visualize a clot or an impedance to flow in a thoracic catheter, which as described above, is a common, recognized, and unresolved problem with the day-to-day management in patients with thoracic catheters. With the disclosed device, a physician can directly visualize any blockage and intervene through irrigation and suction. Additionally, as noted above, this device could act as an entry port for video assisted thoracoscopy surgery. Standard video-assisted thoracoscopy surgery requires three or more ports. This single port option would dramatically decrease patient discomfort and medical and surgical complications.

Additionally, a novel method and device for clearing the catheter of blockage is envisioned. A clearing component of known length is inserted into the catheter to scrape the interior walls of the catheter or otherwise clear the catheter of blockage, preferably with a slight to moderate concurrent negative pressure applied. The head of the clearing component may be, for example, bristle, screw, and/or rotary blade shaped, and will preferably rotate as it is inserted into the catheter. The head will be connected and supported by a flexible linear support body. In a preferred embodiment, the screw or cutting angled component head will preferably, as it rotates, pull the blockage in a direction towards the proximate end of the catheter upon encountering the blockage, whereby the negative pressure will also aid in moving the blockage and any debris out of the catheter and away from the patient. Additionally or alternatively, the head of the cleaning component could have an extendable clasp that grabs hold of the blockage and allows the blockage to be pulled or pulled and/or suctioned out.

The present invention also relates to a thoracic catheter device comprising a distal end with a plurality of holes, with the distal end being designed to be inserted into a human body, and a proximate end remaining exterior to the human body.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which.

DETAILED DESCRIPTION OF THE PREFERRED EMBODIMENTS

The present invention will be understood by reference to the following detailed description, which should be read in conjunction with the appended drawings. It is to be appreciated that the following detailed description of various embodiments is by way of example only and is not meant to limit, in any way, the scope of the present invention.

Figure 1:
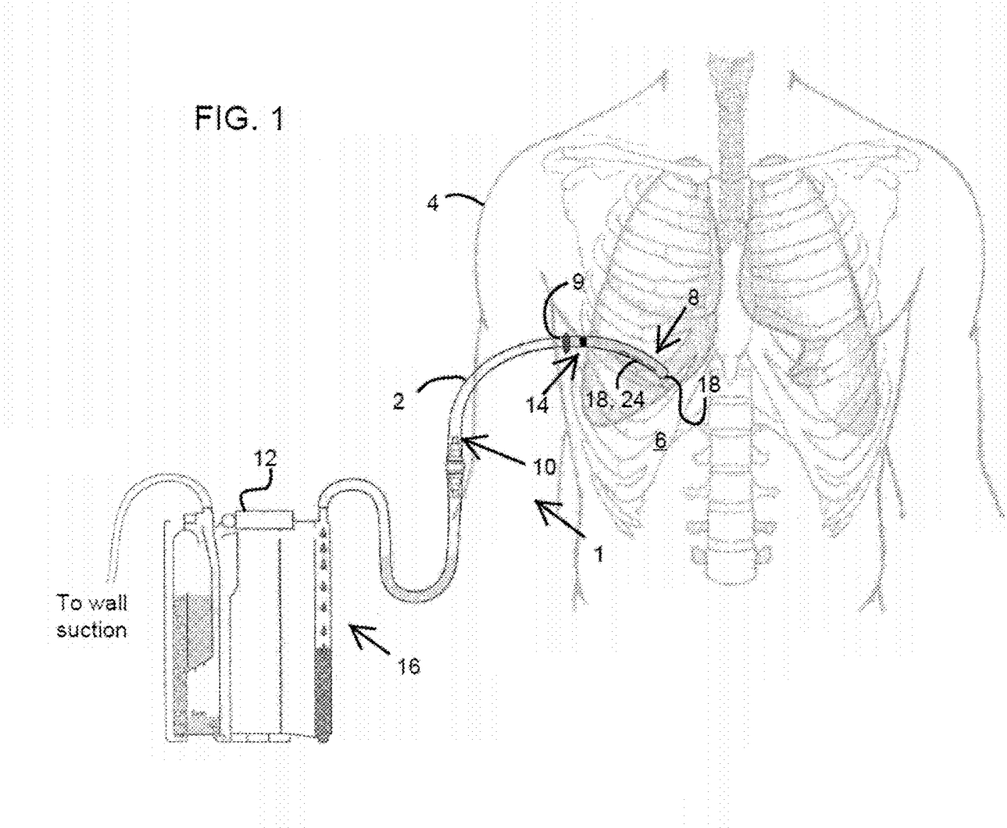
FIG. 1 is a schematic drawing of the thoracic catheter system of the disclosed invention with a distal end of a thoracic catheter inserted into the chest cavity of a patient and a proximate end connected to a suction canister.

Turning now to FIG. 1, a brief description concerning the various components of the present invention will now be briefly discussed. As can be seen in this first embodiment, the invention is a thoracic catheter system 1 comprising a flexible or semi-flexible chest tube or thoracic catheter 2 made from plastic, silicone, rubber, metal, or some combination thereof. A distal end 4 of the thoracic catheter 2 is inserted into the thoracic cavity 6 of the patient 8 through an incision 9, and a proximate end 10 of the thoracic catheter 2 is connected to a suction canister 12 or wall or other suction. The thoracic catheter 2 will preferably include special internal coatings, such as, inter alia, polytetrafluoroethylene ("Teflon"), Tethered-Liquid Perfluorocarbon (comprising a monolayer of perfluorocarbon and a layer of liquid perfluorocarbon), silver ionic, silver nanoparticles, copper, copper alloy, organosilanes, gold, titanium dioxide, and carbon nanotubes, to help prevent clot or blockage 14 formation and/or reduce the risk of infection. The thoracic catheter 2 is inserted into the chest or thoracic cavity 6 in the pleural and/or the pericardial space and is used to remove/evacuate air from the pneumothorax or fluids 16 from such cavities, such as, inter alia, blood, effusion, chyle or pus. The distal end 4 of the thoracic catheter 2 will preferably have one or more apertures 18 extend completely though the side or wall 20 of the thoracic catheter 2.

Figure 2:
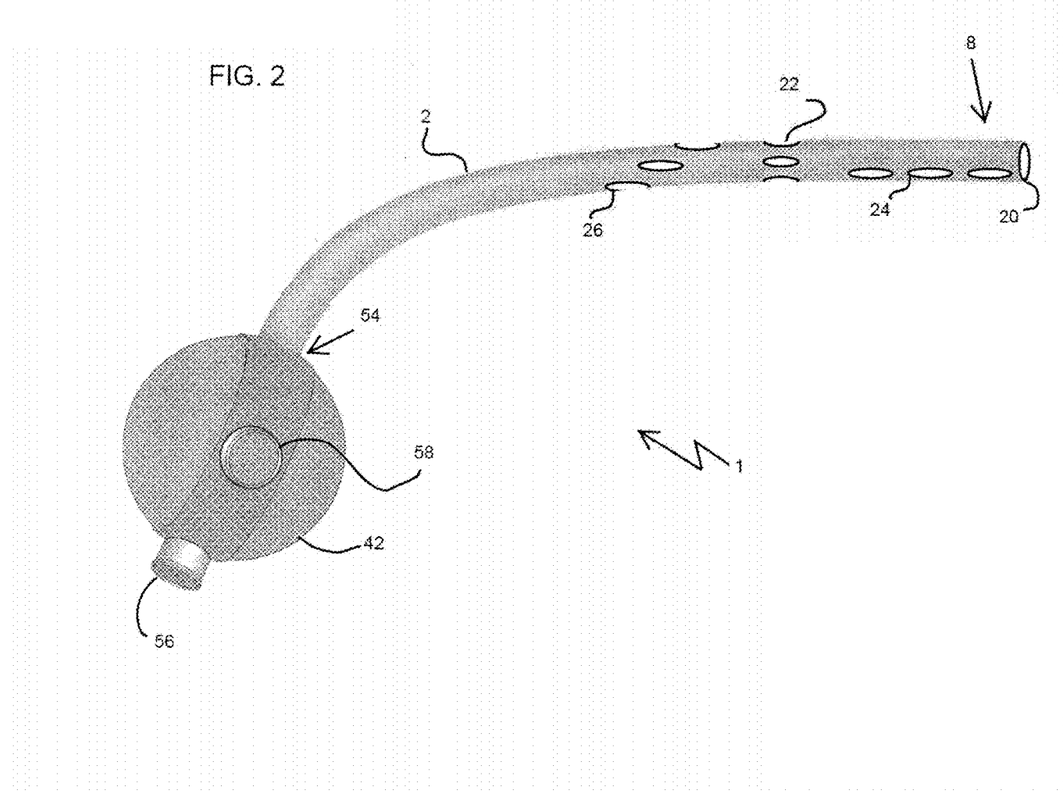
FIG. 2 is a schematic drawing of a second embodiment of the thoracic catheter system including a three way valve.

As shown in FIG. 2, the apertures 18 could be, for example, two, three, four, five, six, or seven in number, and could be preferably positioned radially/circumferentially aligned 22 along a circumference of the thoracic catheter 2, and/or could also be axially aligned 24 along the length of the thoracic catheter 2. Additionally, the apertures 18 could also be in different positions along the thoracic catheter 2, such as helically aligned 26 or some other arrangement. The apertures 18 are preferably large enough to allow an endoscopic camera 28, a suction hose 30, or an endoscopic camera with integrated suction 32 ability (hereinafter collectively referred to as the thoracoscopy device 32) to pass within the thoracic catheter 2 and through such apertures 18.

The thoracoscopy device may also include an integrated irrigation ability 33. A benefit of the circumferentially aligned 22 apertures 18 (preferably in a circumferential grouping of at least three or four apertures 18) in the thoracic catheter 2 is to allow a virtual 360 degree radial view for a camera 28, 32 at a single axial length. The apertures 18 are preferably all the same size, but one or more could be different sized. Further or additional apertures 18 could be added that are too small for the thoracoscopy device 32 to pass through, but which could nonetheless increase the draining ability of the thoracic catheter 2. Among various designs, there could be a single circumferentially aligned 22 group of apertures 18, a single axially aligned 24 group of apertures 18, or multiple groups of axially spaced circumferentially aligned 22 apertures 18 and/or multiple groups of circumferentially spaced axially aligned 24 apertures 24. A further embodiment provides for multiple helical groups 26 of apertures 18, where at least two helixes 26 are circumferentially aligned, so as to provide at least partially the advantages of both circumferentially aligned 22 and axially aligned 24 aperture 18 groupings. The arrangement of apertures 18 in the thoracic catheter 2 could be chosen for both maximal drainage of the thoracic cavity 6 and maximal accessibility with the thoracoscopy device 32.

Figure 4:
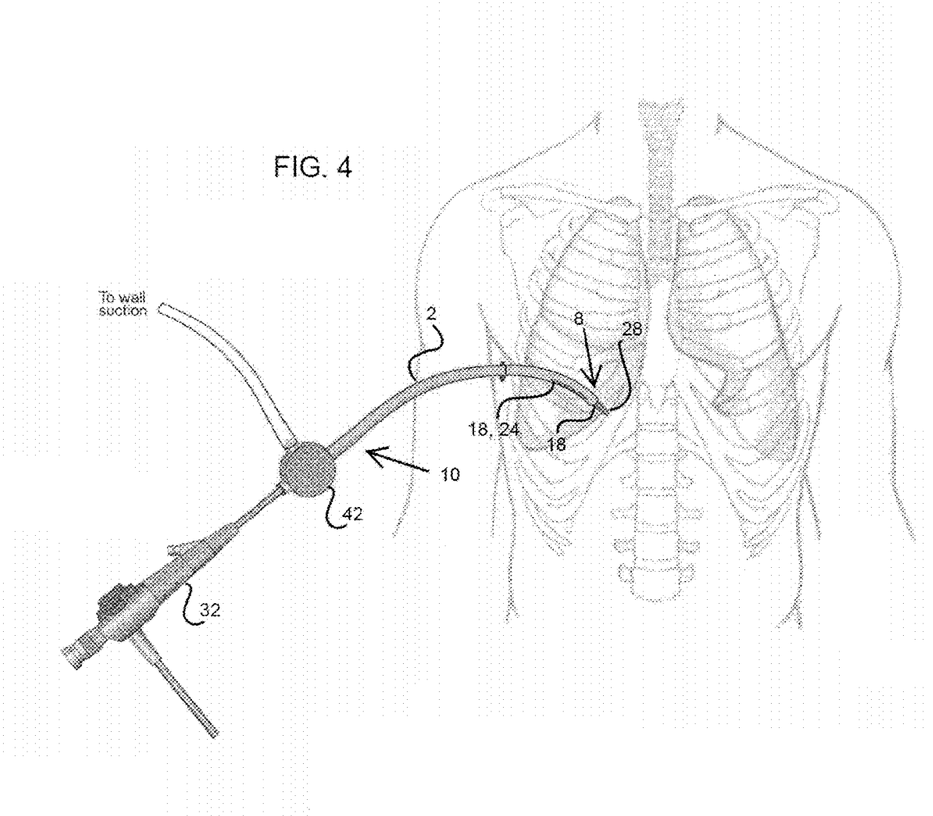
FIG. 4 is a schematic drawing of the system in FIG. 3, wherein the thoracoscopy device is inserted in and through the three way valve and through the thoracic catheter and extends out a terminal hole in the distal end of the thoracic catheter into the thoracic cavity of the patient.
Figure 5:
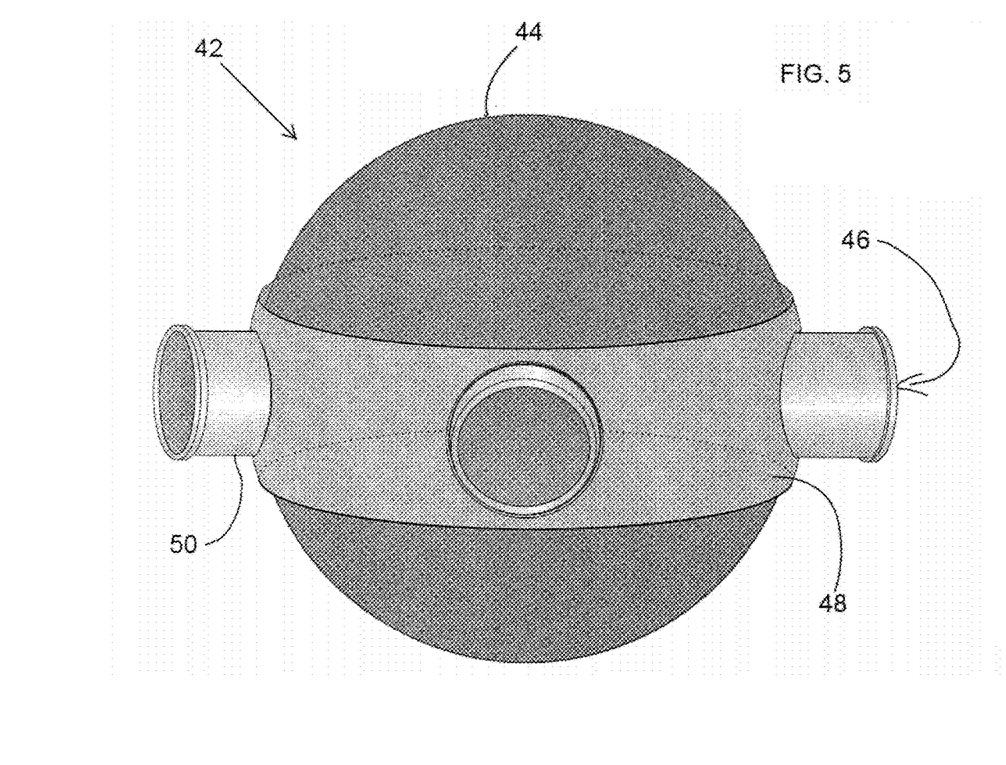
FIG. 5 is a partial see-through diagrammatic front view of the three way valve of FIGS. 3 and 4.
Figure 6:
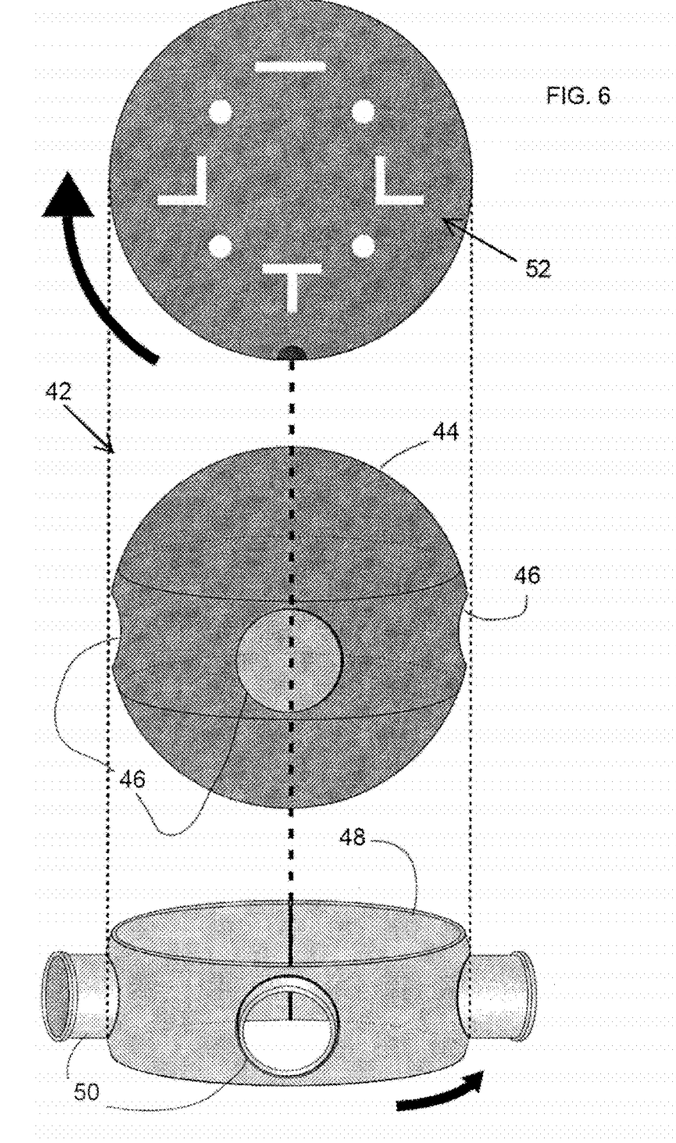
FIG. 6 is an exploded view of the three way valve of FIG. 5 in a first stable open position where all three external ports on the outer collar are aligned with a respective through hole in the hollow body.
Figure 7:
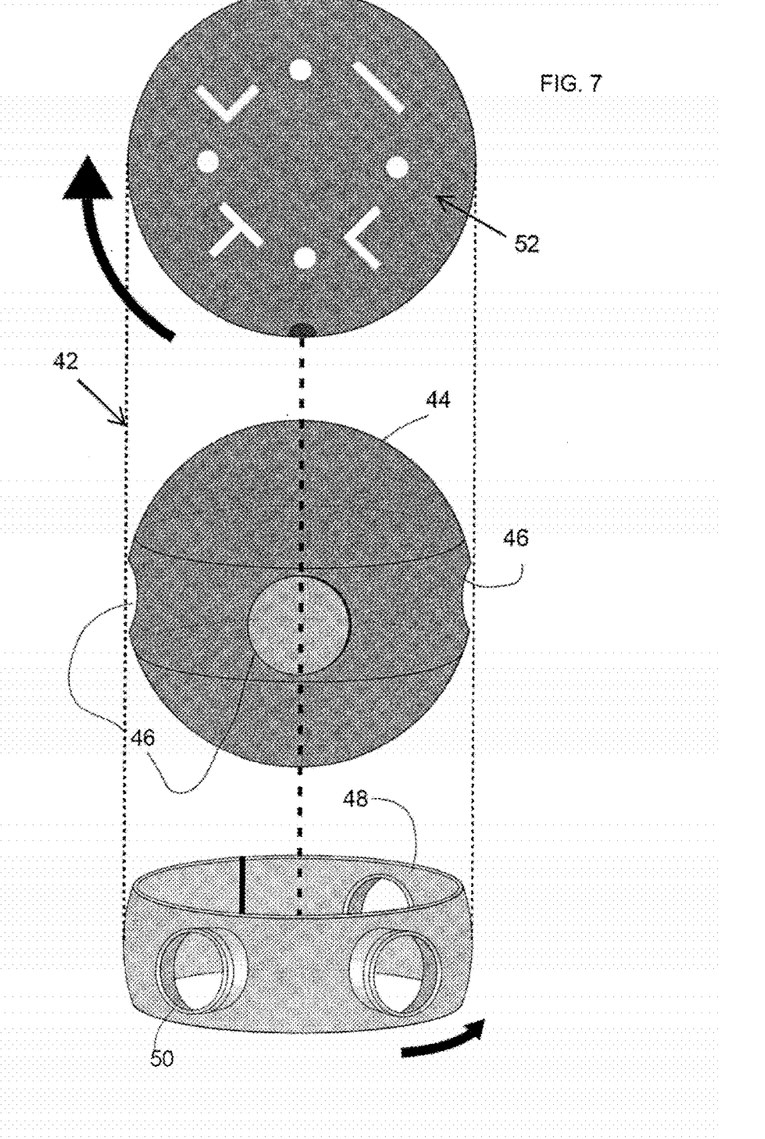
FIG. 7 is an exploded view of the three way valve of FIG. 5 in a first stable closed position, 45 degrees from the first stable open position, where all three external ports on the outer collar are closed off from all of three through holes in the hollow body.
Figure 8:
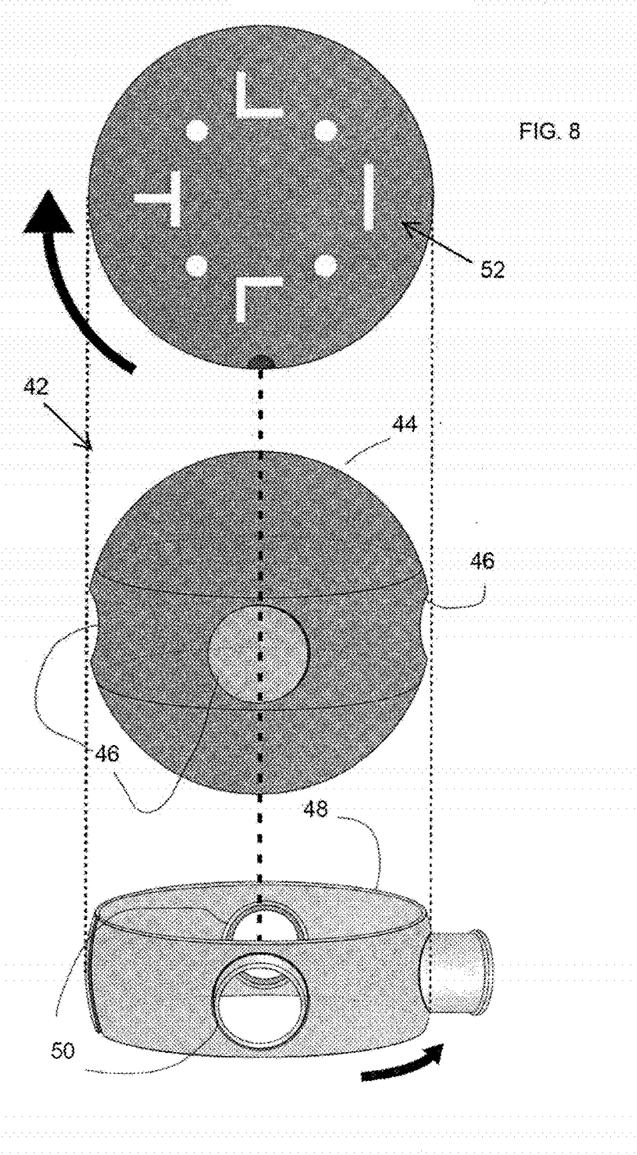
FIG. 8 is an exploded view of the three way valve of FIGS. 3 and 4 in a second stable open position, 90 degrees from the first stable open position, where the front and the right side through holes in the hollow body, with respect to the figure, are aligned with a respective external port on the outer collar, and the left side through hole in the hollow body, with respect to the figure, is aligned with a solid surface of the collar, and thus fluidly closed, and a third external port is aligned with a solid surface of the back of the hollow body, with respect to the figure, and thus fluidly closed.
Figure 9:
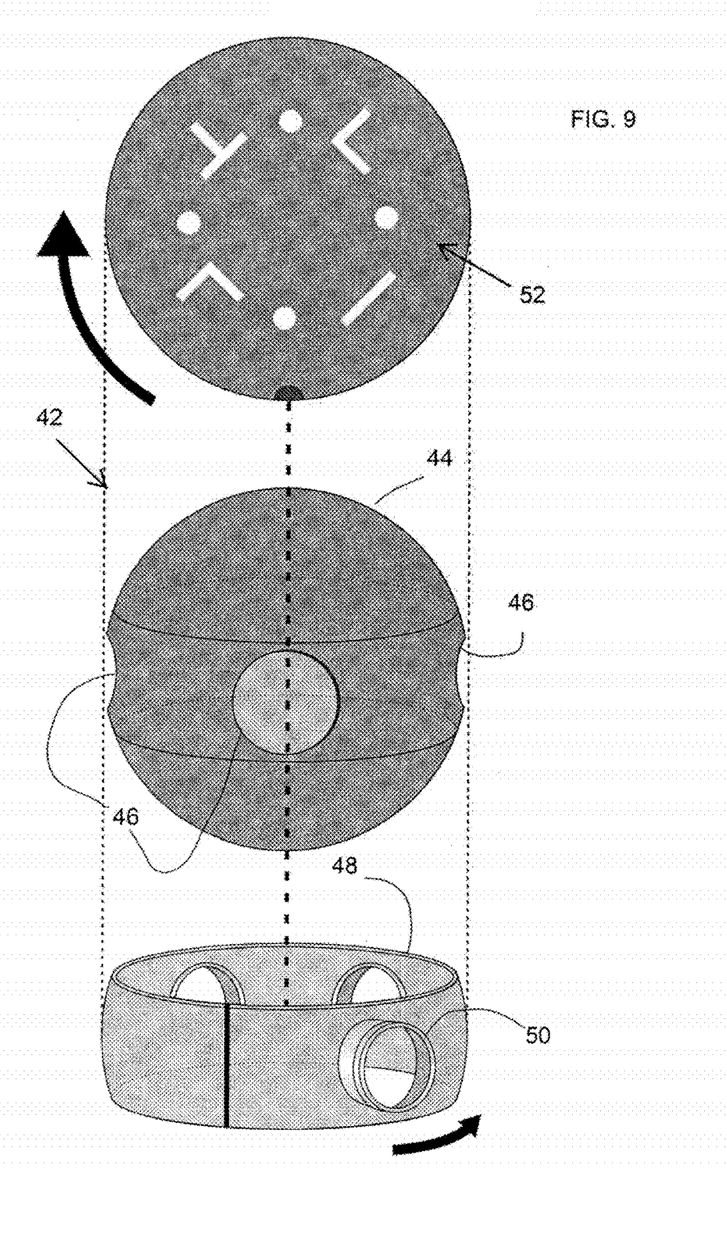
FIG. 9 is an exploded view of the three way valve of FIG. 5 in a second stable closed position, 90 degrees from the first stable closed position and 45 degrees from the second stable open position, where all there external ports on the outer collar are closed off from all of the through holes in the hollow body.
Figure 10:
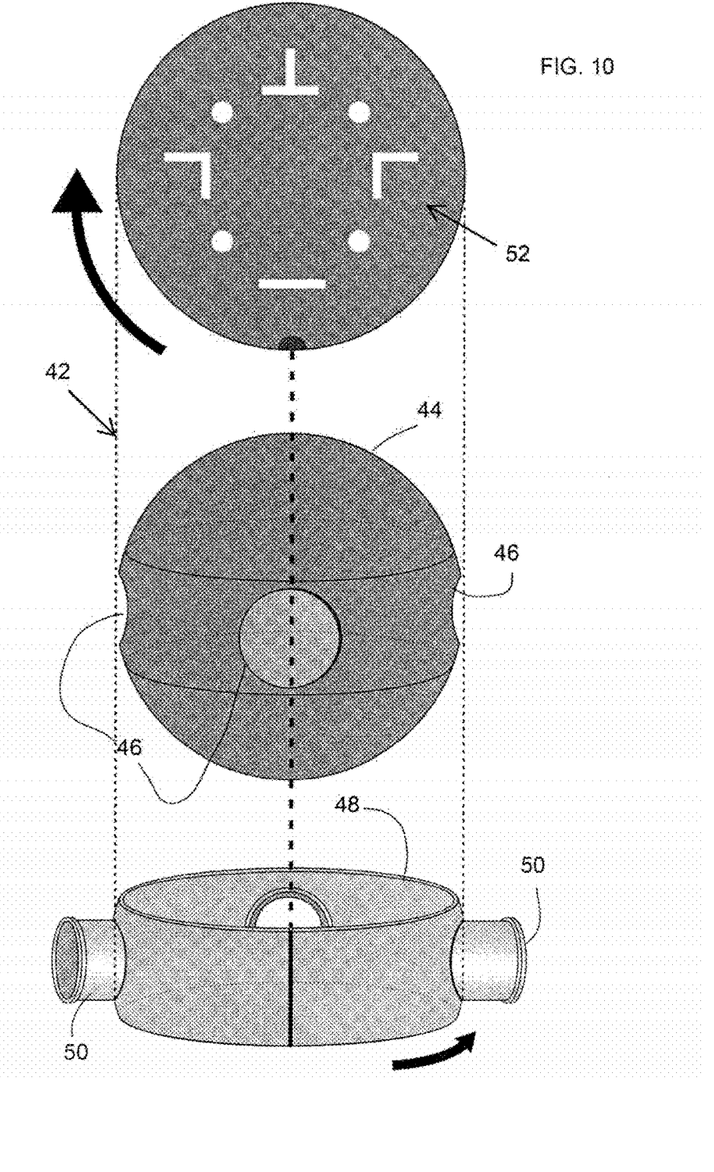
FIG. 10 is an exploded view of the three way valve of FIG. 5 in a third stable open position, 90 degrees from the second stable open position, where the left side and the right side through holes in the hollow body, with respect to the figure, are aligned with a respective external port on the outer collar, and the front through hole in the hollow body, with respect to the figure, is aligned with a solid surface of the collar, and thus fluidly closed, and a third external port is aligned with a solid surface of the back of the hollow body, with respect to the figure, and thus fluidly closed.
Figure 11:
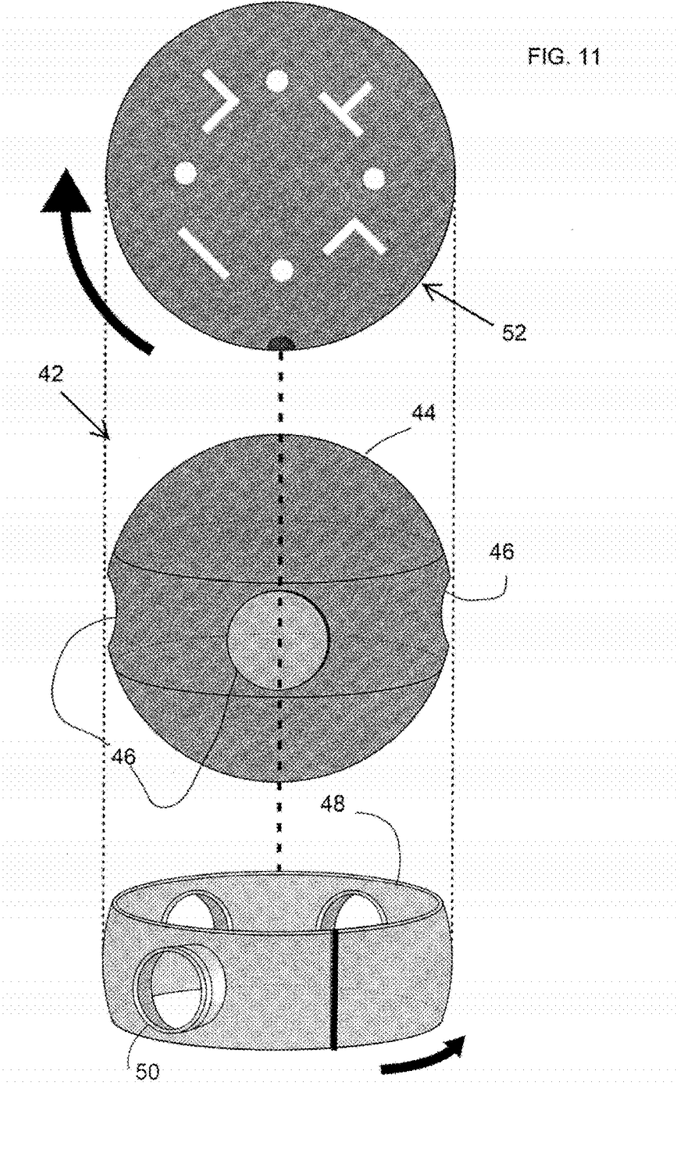
FIG. 11 is an exploded view of the three way valve of FIG. 5 in a third stable closed position, 90 degrees from the second stable closed position and 45 degrees from the third stable open position, where all there external ports on the outer collar are closed off from all of the through holes in the hollow body.
Figure 12:
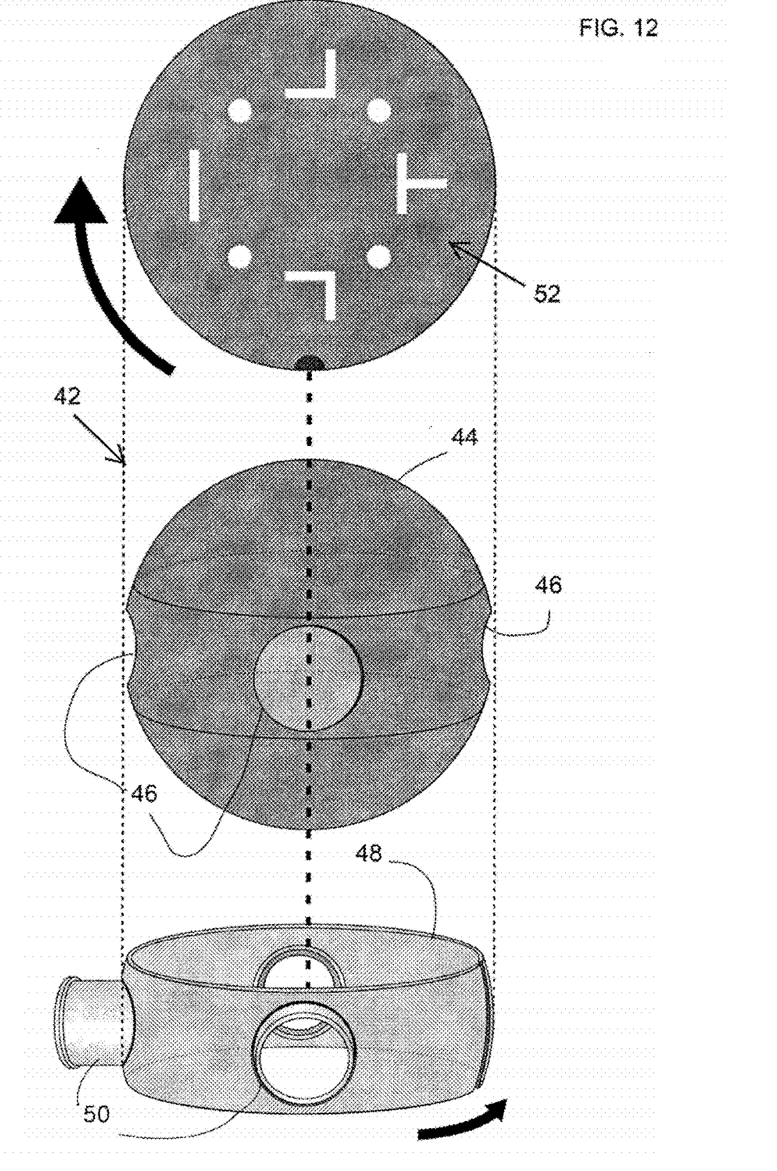
FIG. 12 is an exploded view of the three way valve of FIG. 5 in a fourth stable open position, 90 degrees from the third stable open position, where the front and the left side through holes in the hollow body, with respect to the figure, are aligned with a respective external port on the outer collar, and the right side through hole in the hollow body, with respect to the figure, is aligned with a solid surface of the collar, and thus fluidly closed, and a third external port is aligned with a solid surface of the back of the hollow body, with respect to the figure, and thus fluidly closed.
Figure 13:
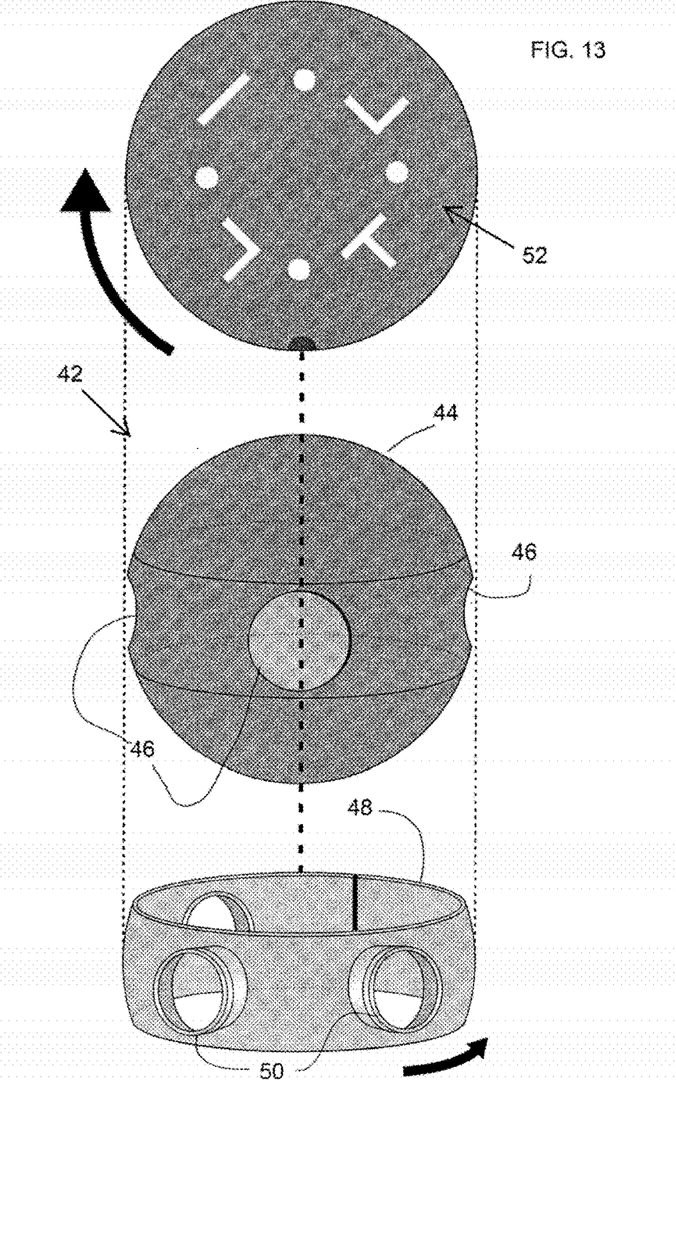
FIG. 13 is an exploded view of the three way valve of FIG. 5 in a fourth stable closed position, 90 degrees from the third stable closed position and 45 degrees from the fourth stable open position, where all there external ports on the outer collar are closed off from all of the through holes in the hollow body.

The terminal/distal end 4 of the thoracic catheter 2 is preferably open with an aperture 18, which also allows the thoracoscopy device 32 to pass through such distal end 4, as shown in FIG. 4. The passage of the thoracoscopy device 32 not only helps with unclogging the thoracic catheter 2, it also helps a physician to visualize and thus reposition the thoracic catheter 2 as needed. The camera 28 of the thoracoscopy device 32 would allow the physician operator to visualize inside the pleural and/or the pericardial cavities in the thoracic cavity 6 and even perform biopsy where required. The operator could reposition the thoracoscopy device 32, use the set-up for drug delivery, contrast delivery, interventional radiology procedures, and pleurodesis. This could also provide access to the mediastinum and could be used as an alternative approach for conducting a mediastinoscopy. With the information gathered by non-invasive imaging (e.g., chest-x-rays and CT) and video-endoscopy, the operator could visualize and recognize malposition of the thoracic catheter 2 and a cause for blockage 14 if such is present. This would allow the operator to reposition and unblock the thoracic catheter 2 immediately. The thoracoscopy device 18 could additionally have biopsy functionality, or a similarly sized thoracoscopy biopsy instrument could be used. This would also provide a method to obtain microbiology specimens and/or biopsy of the lung and or pleura or mediastinum through the single thoracic catheter 18, without starting an additional chest tube into the patient 8.

A second embodiment of the thoracic catheter system 1, as shown in FIG. 2, includes a three way valve 42 which is one of fused/permanently attached and removably attached to the outer proximate end 10 of the thoracic catheter 2.

One embodiment of the three way valve or medical stopcock 42 consists of a chamber part or hollow body 44, with three through holes 46 of preferably equal diameter at 90° degree intervals along a circumference of the hollow body 44. While the hollow body 44 is shown in the shape of a sphere, it may also have the shape of an oblate spheroid, a prolate spheroid or a cylinder, for example. An inner surface of the hollow body 44 is preferably a smooth sphere, spheroid, or cylinder, except for the through holes 46 extending through the wall of the hollow body 44. An outer ring 48 with the external ports 50 is placed around the hollow body 44 perimeter. The outer ring 48 can be rotated around the hollow body 44, or, conversely, the hollow body 44 can be rotated within the outer ring 48. The external ports 50 are preferably be rotated with the outer ring 48 with respect to the hollow body 44, as shown in FIGS. 5-13, to allow for all three external ports 50 to open or closed as needed. When an external port 50 is rotationally aligned with a through hole 46, a fluid connection is established between the external port 50 and the interior of the hollow body 44 and the external port 50 can be considered open or on. When an external port 50 is fully rotationally spaced from any through hole 46, that external port 50 is fluidly isolated from the interior of the hollow body 44 and that external port 50 can be considered fluidly closed or in an off position. On the exterior of the hollow body 44 are preferably indicia to readily indicate the position of the through holes 46 with respect to the external ports 50, like raised bumps or other visual or tactile indicators on the exterior surface of the hollow body 44 aligned with each through hole 46, the through holes 46 being normally visually concealed by the outer ring 48. Additionally there can be a flow path indicator 52 that shows which external ports 50 are fluidly connected to the interior of the hollow body 44 with a given relative rotation of the hollow body 44 and the outer collar 48. This embodiment of the three way valve 42 has markings that clearly show the 8 rotationally stable on/off positions of the shown embodiment of the three-way valve 42. The indicia and/or flow path indicator 52 eliminates the confusion of the older technology of three way valves 42 in the art with a single "off position." The three way valve 42 is further described in PCT Patent Appln. No. PCT/US2015/012593 filed Jan. 23, 2015, the contents of which are incorporated herein by reference in its entirety.

Figure 3:
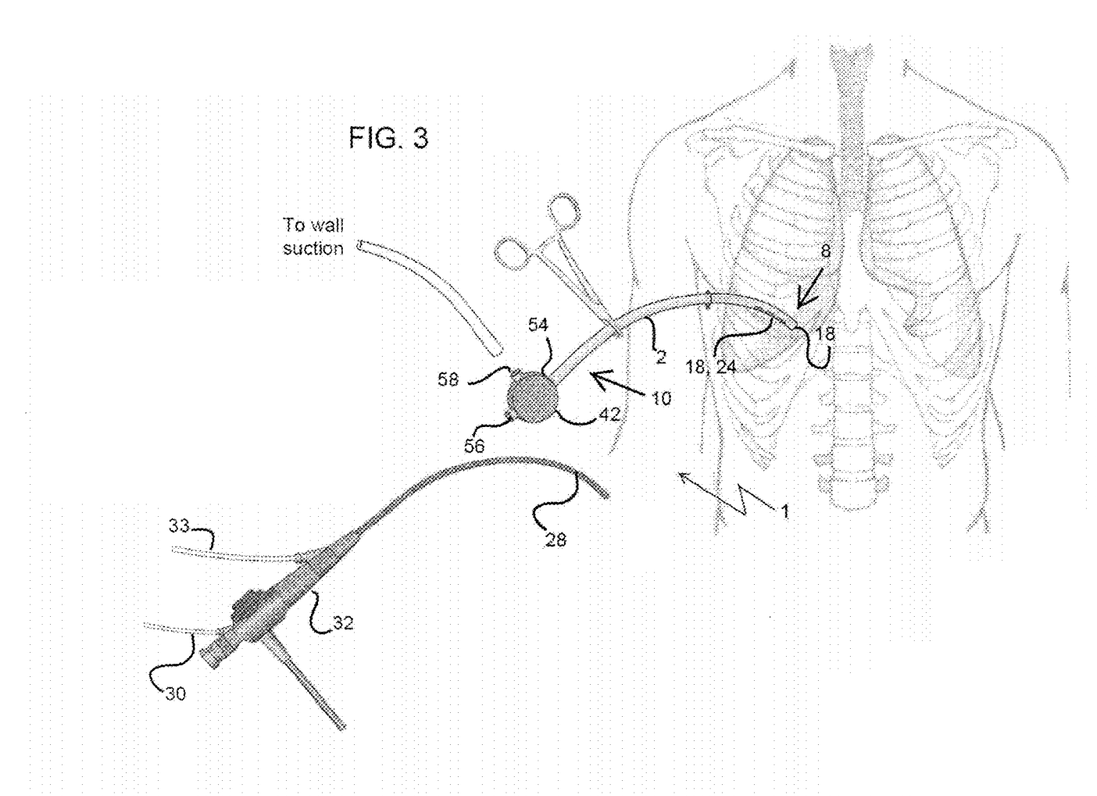
FIG. 3 is a schematic drawing of the thoracic catheter system according to FIG. 1, connected to the three way valve similar two FIG. 2, further including a thoracoscopy device and further connection to wall suction.

When the above three valve filter 42 is used with the thoracic catheter 2, as shown in FIGS. 2-4, the three external ports 10 may be termed branch tubes 10, including a downstream branch-tube 54, which is preferably part of the external or proximate section 10 of the thoracic catheter 2, an upstream branch-tube 56, which is axially aligned with the downstream branch-tube 54, and a merge-branch-tube 58, preferably orthogonal to the downstream branch-tube 52. All three branch tubes 10 extend from the hollow body 44. One or more of the branch tubes 10 may further include a single direction flow valve (not shown). In the situations where the thoracoscopy device 32 equipped with the suction hose 30 is to be inserted in the patent 4, as shown in FIGS. 3 and 4, one branch tube 10, preferably the merge-branch tube 58, would preferably be connected to the wall suction and a second branch tube 10, preferably the upstream branch tube 56, would be used for insertion of the thoracoscopy device 32 into the three way valve 42 and a third branch tube 10, preferably the downstream branch-tube 54, would be used for the thoracoscopy device 32 to access the thoracic catheter 2, and via the thoracic catheter 2, the patient's thoracic cavity 6.

Returning to FIGS. 3 and 4, a preferred embodiment of the thoracic catheter system 1 would have two components including the disposable thoracic catheter device (equipped with the three way valve 42) and the thoracoscopy device 32 which is purposefully designed to work with the thoracic catheter system 1. The thoracoscopy device 32 (including a camera equipped with a strong suctioning and flushing capability) would preferably be designed for this purpose and could be sterilized and reused. The disclosed system would make the thoracic catheters 2 more efficient and durable and/or salvageable in the event of clogging 14. The incision site 9 of the thoracic catheter 2 could be used as a port 9 of entry when performing the VATS procedures (e.g., VATS talc pleurodesis, VATS decortications, etc.). The functionality of the above three way valve 42 would allow the thoracoscopy device 32 to be easily inserted into the thoracic catheter 2 to check blockage 14 and remove blockage 14 if present, while still maintaining wall suction if desired. Also, the ability to fully remove the thoracoscopy device 32 from the thoracic catheter 2, while still maintaining wall suction, allows for other therapeutic or diagnostic procedures to be inserted/conducted via the upstream branch tube 56.

The disclosed thoracic catheter device 2 would preferably be packaged in a sterile container, stored on the operating room shelf, in the wards or in the ER, and opened when needed. The thoracic catheter devices could come in different sizes (for pediatric and adult patients). It is anticipated that physicians and surgeons would use the thoracic catheter devices whenever deciding to insert a thoracic catheter, or after making the incisions during a VATS procedure, or any other cardiac or thoracic surgeries.

In use, it is anticipated that the thoracic catheter device 2 would be given to the physician by the circulating nurse. The physician would insert the thoracic catheter device 2 with the three way vale 42 extension outside of the patient body 4 and the sterile thoracoscopy device 32 camera 28 rolling inside the thoracic catheter device 2. On a side-way of the three-way valve 42, a suction 12 is attached. There is preferably also a suction extension adjusted on the thoracoscopy device camera itself.

The consumers for this device would be hospitals (operation rooms, interventional radiology suits, wards, and emergency room), ambulatory clinics, outpatient settings, ambulances, and paramedic facilities which perform thoracic catheter 2 insertion for hemo- or pneumothorax in traumatic and non-traumatic settings (including but not limited to pulmonary diseases such as cancer, infectious disease, or collagen vascular diseases). It would also be targeted for use by facilities that perform cardiothoracic surgeries (coronary artery bypass graft, heart valve surgeries, intrathoracic lung surgeries, VATS procedures, etc.). This device aims to make thoracic catheters 4 more efficient, more durable and ultimately make clogged 14 tubes 2 salvageable without limiting the flow of the thoracic catheter 2, and reducing the risk of infection, making the detection of any tube 2 malfunction easier, and make changing of the proximate end 10 catheter 2 tip position easier. This thoracic catheter system 1 will spare the patient 4 from having multiple procedures and/or multiple thoracic catheters 2 inserted. The operations would become more efficient, saving operating room time, and decreasing the recurrence of pleural effusion or pneumothorax or hemothorax in the patient 4. The novel three way valve 42 portion of the thoracic device 2 disclosed will also allow for substantially easier usage and camera 28 placement.

While various embodiments of the present invention have been described in detail, it is apparent that various modifications and alterations of those embodiments will occur to and be readily apparent to those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having," and variations thereof herein, is meant to encompass the items listed thereafter and equivalents thereof as well as additional items while only the terms "consisting of" and "consisting only of" are to be construed in a limitative sense.

Where a definition or use of a term in a reference, which is incorporated by reference herein, conflicts or is contrary to the definition or use of that term provided herein, the definition or use of that term provided herein applies and the definition or use of that term in the reference does not apply.

Wherefore, we claim:

1. A thoracic catheter system comprising:
a flexible thoracic catheter for inserting into a thoracic cavity of a human;
a distal end of the thoracic catheter has a plurality of apertures; and
a proximate end of the thoracic catheter designed to extend out of the thoracic cavity; and
a three way valve that is one of fused with and removably attached to the proximate end of the thoracic catheter,
wherein the three way valve includes an outer ring extending around a circumference of a body of the three way valve, the outer ring defining multiple external ports, and the outer ring may be rotated with respect to the body to open and close one or more of the multiple external ports; and
wherein the three way valve has four stable on positions and four stable off positions.

2. The thoracic catheter system of claim 1 further comprising a first set of the plurality of apertures being one of axially aligned along an elongate axis defined by an elongate length of the thoracic catheter, radially aligned along a circumference of the thoracic catheter, and helically aligned along the circumference of the thoracic catheter and the elongate axis.

3. The thoracic catheter system of claim 2 further comprising a second set of the plurality of apertures being one of axially aligned along the elongate axis, radially aligned along the circumference of the thoracic catheter, and helically aligned along the circumference of the thoracic catheter and the elongate axis.

4. The thoracic catheter system of claim 3 further comprising the first set of the plurality of apertures being one of radially spaced and axially aligned, axially spaced and radially aligned, and both radially spaced and axially spaced from the second set of the plurality of apertures.

5. The thoracic catheter system of claim 1 further comprising at least a first portion of the plurality of apertures being sized to allow passage of a thoracoscopy device camera.

6. The thoracic catheter system of claim 5 further comprising at least a second portion of the plurality of apertures being sized of a smaller diameter than the first portion of the plurality of apertures, the second portion of the plurality of apertures being sized too small to allow passage of a thoracoscopy device camera, but of sufficient diameter to allow drainage of the thoracic cavity.

7. The thoracic catheter system of claim 1 further comprising a terminal through opening in a terminal portion of the distal end, the through opening being aligned with an elongate axis defined by an elongate length of the thoracic catheter.

8. The thoracic catheter system of claim 1 wherein a terminal through opening is sized to allow passage of a thoracoscopy device camera.

9. The thoracic catheter system of claim 1 further comprising an inner surface of the thoracic catheter being formed of one of polytetrafluoroethylene, Tethered-Liquid Perfluorocarbon, silver ionic, silver nanoparticles, copper, copper alloy, organosilanes, gold, titanium dioxide, and carbon nanotubes.

10. The thoracic catheter system of claim 1 further comprising the thoracic catheter being formed of one of plastic, silicone, rubber, and metal.

11. The thoracic catheter system of claim 1 further comprising a thoracoscopy device.

12. The thoracic catheter system of claim 11 wherein the thoracoscopy device includes one of a suctioning capability, a flushing capability, and a camera.

13. A method of accessing thoracic cavity of a patient to provide therapy comprising:
inserting a flexible thoracic catheter into a thoracic cavity of a human;
wherein a distal end of the thoracic catheter has a plurality of apertures;
a proximate end of the thoracic catheter extends out of the thoracic cavity; and
a three way valve is one of fused with and removably attached to the proximate end of the thoracic catheter, and the plurality of apertures are radially aligned along a circumference of the thoracic catheter;
wherein the three way valve has four stable on positions and four stable off positions.

14. The method of claim 13 further comprising the step of draining one of a solid, a liquid, and a gas from the thoracic cavity of the patient through the thoracic catheter.

15. The method of claim 13 further comprising the step inserting a thoracoscopy device with a camera through the three way valve into the thoracic catheter to visualize any blockage in the thoracic catheter.

16. The method of claim 15 further comprising the thoracoscopy device having one of a suctioning and a flushing capability, and one of flushing or suctioning a blockage out of the thoracic catheter with the thoracoscopy device.

17. The method of claim 13 further comprising the step inserting a thoracoscopy device directly into a thoracic cavity of the patient through one of a terminal through opening in a terminal portion of the distal end and one of the plurality of apertures.

18. The method of claim 13 further comprising the step of conducting a video-assisted thoracoscopic surgery through a single port where the single port is the thoracic catheter.

19. A thoracic catheter system comprising:
a flexible thoracic catheter for inserting into a thoracic cavity of a human;
a distal end of the thoracic catheter has a plurality of apertures; and
a proximate end of the thoracic catheter designed to extend out of the thoracic cavity; and
a three way valve that is one of fused with and removably attached to the proximate end of the thoracic catheter;
wherein an inner surface of the thoracic catheter is formed of one of polytetrafluoroethylene, silver ionic, silver nanoparticles, copper, copper alloy, organosilanes, gold, titanium dioxide, and carbon nanotubes;
wherein the three way valve has four stable on positions and four stable off positions.

* * * * *